United States Patent [19]

Via et al.

[11] 4,126,650
[45] Nov. 21, 1978

[54] SYNTHESIS OF MONO-ALKYL ACID PHOSPHATES WITH HIGH MONO-CONTENT

[75] Inventors: Francis A. Via, Yorktown Heights, N.Y.; Sophia Y. Liu, Fremont, Calif.

[73] Assignee: Stauffer Chemical Company, Westport, Conn.

[21] Appl. No.: 791,625

[22] Filed: Apr. 27, 1977

[51] Int. Cl.² .................................................. C07F 9/09
[52] U.S. Cl. ................................................... 260/980
[58] Field of Search ......................................... 260/980

[56] References Cited

U.S. PATENT DOCUMENTS

| | | | |
|---|---|---|---|
| 3,318,982 | 5/1967 | Klose et al. | 260/980 |
| 3,333,029 | 7/1967 | Müller-Schiedmayer et al. | 260/980 |

Primary Examiner—Anton H. Sutto
Attorney, Agent, or Firm—William R. Robinson

[57] ABSTRACT

Mono-alkyl acid phosphates having the formula:

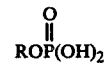

wherein R is straight or branched alkyl having from 1 to about 25 carbon atoms, are prepared by reacting alcohol with $P_2O_5$. The process involves suspension of $P_2O_5$ in a heel of product comprised of a mixture of mono-alkyl acid phosphate, di-alkyl acid phosphate and free $H_3PO_4$. Alcohol is added to the heel last, followed by mixing, and then addition of water. A mixture of mono- and dialkyl acid phosphate is obtained with a mono-content of over about 70 percent by weight.

5 Claims, No Drawings

SYNTHESIS OF MONO-ALKYL ACID PHOSPHATES WITH HIGH MONO-CONTENT

BACKGROUND OF THE INVENTION

1. Field of the Invention

The present invention relates, in general, to a method of preparing mono-alkyl acid phosphates and, particularly, concerns an improved method of preparing said phosphates with a high mono-content.

2. The Prior Art

Mono-alkyl acid phosphates are well-known, and are generally prepared by reacting alcohols with phosphorus pentoxide. The nature of the chemical reaction between alcohols and phosphorus pentoxide is very non-discreet. The result, therefore, is a mixture of products including mono-alkyl acid phosphate, di-alkyl acid phosphate, free phosphoric acid, variously substituted pyrophosphate, and, possibly even triphosphate. The situation is further complicated in the case wherein stearyl alcohol is used as it is a solid at room temperature and relatively unreactive. Phosphorus pentoxide is also a solid. Therefore, the reaction between stearyl alcohol and phosphorus pentoxide must be run at a temperature above the melting point of stearyl alcohol (mp 58° C.).

It is particularly advantageous to obtain a product according to the present invention that is high in mono-content. The high mono-content product is more effective than low mono-content products as a surfactant and as an agent for removal of blood stains, egg yolk, and the like from cloth and other materials.

Various methods have been described in the prior art for improving the mono-content in the synthesis of mono-alkyl acid phosphates. In U.S. Pat. No. 2,586,897 for example, water is added to the reaction mixture of lauryl alcohol and phosphorus pentoxide to hydrolyze any acid phosphate esters. This enhances the production of monolauryl phosphate. This technique is also described in U.S. Pat. No. 3,318,982.

It is also known in the prior art to add hydrogen peroxide to the reaction mixture to improve the color of the product.

SUMMARY OF THE INVENTION

In accordance with the present invention, production of mono-alkyl acid phosphates with high mono-content is achieved by following a specific reaction sequence. The sequence comprises suspension of $P_2O_5$ in a heel of product comprised of a mixture of mono-alkyl acid phosphate, di-alkyl acid phosphate, and free $H_3PO_4$. Alcohol is added to the heel last, followed by mixing. Water is then added to the mixture. Hydrogen peroxide can also be added to improve color of the product. The product is a mixture of mono- and di-alkyl acid phosphate having a mono-content of over about 70 percent by weight.

The products of the present invention have the general formula:

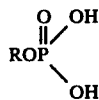

wherein R is straight or branched alkyl having from 1 to about 25 carbon atoms.

A highly idealized reaction scheme for the present invention is:

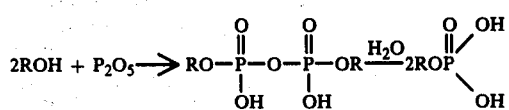

wherein R is as defined above.

DETAILED DESCRIPTION OF THE INVENTION

A first preparation of mono-alkyl acid phosphate is conducted according to standard procedures to obtain a heel for subsequent preparations pursuant to the process of this invention. This heel is defined as the reaction product of a reaction to prepare mono-alkyl acid phosphate. The majority of the heel is therefore mono-alkyl acid phosphate and the remaining portion is the impurities produced in the reaction, primarily di-alkyl acid phosphate and free $H_3PO_4$. This preparation is conducted by simply reacting alkyl alcohol with phosphorus pentoxide in the presence of water and hydrogen peroxide. The reaction is conducted according to the following general reaction scheme:

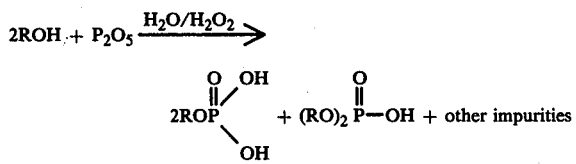

wherein R is straight or branched alkyl having from 1 to about 25 carbon atoms. Exemplary R groups include, but are not limited to methyl, ethyl, propyl, isopropyl, butyl, tert-butyl, pentyl, heptyl, octyl, decyl, dodecyl, hexadecyl, nonadecyl, lauryl, palmityl and stearyl.

The heel from this first preparation is subsequently utilized in the process of the present invention which comprises suspending phosphorus pentoxide in the heel followed by the addition of alcohol and then mixing. This process is conducted at a temperature from about 20° C. to about 180° C., and preferably from about 50° C. to about 100° C. The preferred temperature range is selected because excess thermal energy will promote undesirable side reactions such as dehydration which results in the formation of pyro-compounds. Inadequate thermal energy, however, can result in crystallization or solidification of the alcohol. Process temperatures that will provide good viscosity for ease of mixing and good product distribution can easily be determined by one skilled in the art.

Water is then added to the reaction mixture, and hydrogen peroxide can also be added as an option to improve color of the product. The reaction mixture is then maintained at a temperature from about 40° C. to about 200° C., and preferably from about 60° C. to about 140° C. The reason for the preference is to minimize thermal catalyzed degradation which is accompanies by lower yields, undesired product color even with the addition of hydrogen peroxide; and possible loss of desired product selectivity. The optimum temperature can easily be determined by one skilled in the art.

The product is a mixture of mono-alkyl acid phosphate and di-alkyl acid phosphate having a mono-content of over about 70 percent by weight.

Exemplary alcohols that can be utilized in accordance with the present invention include, but are not limited to methanol, ethanol, propanol, butanol, stearyl alcohol, and lauryl alcohol.

The reaction can be conducted in a continuous or batch-wise process.

Reaction times can vary over relatively wide ranges and can easily be determined by one skilled in the art. Factors affecting reaction time include reaction temperature, viscosity, efficiency of mixing, rate of addition of reactants and rate of heat input. The effects of these variables are demonstrated in the Examples in the present specification.

Typical reaction times are from about 1 to about 10 hours. Times from about 3 to about 6 hours are preferred, however, to prevent product degradation and color formation.

The heel of the reactions is continuously re-used in subsequent reactions.

The products of the present invention can be purified if desired by conventional means. These include crystallization and chromatography among others.

The identification of the products can be achieved by infrared spectroscopy, hydrogen and phosphorus nuclear magnetic resonance spectroscopy, titration, and elemental analysis.

Typical yields of the desired mono-alkyl acid phosphates of the present invention are from about 70 percent to about 95 percent.

Illustrative of the mono-alkyl acid phosphate comounds of the present invention are:

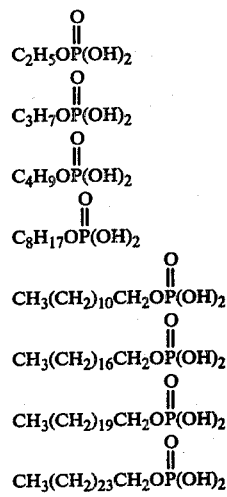

Isomers of the foregoing illustrative compounds are also illustrative of the mono-alkyl acid phosphate compounds of the present invention.

The mono-alkyl acid phosphates of the present invention are useful as surface active agents for use in cleaning systems such as detergents utilized in dish-washing and industrial bottle-cleaning formulations, food grade lubricants and flotation and suspending agents.

One aspect of the present invention involves the preparation of monostearyl acid phosphate. The reaction to produce this product requires the use of molten stearyl alcohol in the process described above, or use of solid stearyl alcohol flakes added to the reaction mixture.

The present invention will be more fully illustrated in the examples which follow.

EXAMPLES

EXAMPLE 1

A first preparation to obtain a heel was conducted as follows:

121.5 grams of stearyl alcohol was added to a reactor provided with a heating mantle and melted at 60°–65° C. When the alcohol was partially melted, gentle stirring was applied to speed up the melting process. Time for complete melting was 20 minutes. The liquid alcohol was clear and colorless.

36.6 grams of phosphorus pentoxide was poured into an Erlenmeyer flask attached by a flexible connector to the reactor. The heating mantle was lowered away from the reactor. With the stearyl alcohol at 61° C., the first half of the phosphrus pentoxide was added at a steady rate over a period of 5 minutes with gentle stirring. The reaction was exothermic reaching a high temperature of 83° C. The reaction mixture, initially clear and colorless was suspended phosphorus pentoxide particles, gradually turned yellow as the temperature rose.

The reaction mixture was stirred for 5 to 10 minutes until the temperature decreased to 70° C. The second half of the addition reaching a temperature of 80° C.

The heating mantle was then raised and the reaction mixture was stirred vigorously at 85° C.

At the end of 2 hours, the mixture was light brown and had increased in volume to about 40 milliliters. 2.1 grams of distilled water, followed by 1.5 gram of 30 percent hydrogen peroxide, was then added. This addition took 1 to 2 minutes. No exotherm was observed.

EXAMPLE 2

50 grams of the heel from Example 1 was added to a round-bottom flask provided with a heating mantle and melted at 60°–65° C. with no stirring. As the heel melted, air bubbles, which had been trapped in the solid product, were observed to rise to the surface and dissipate, resulting in a clear brown melt. The time required to melt the heel was 15 minutes.

Phosphorus pentoxide, 35.5 grams, was then charged into an Erlenmeyer flask with a $\mathbf{5}$ joint which was attached to a flexible connector fitted in one neck of the round-bottom flask. With the heating mantle still raised to maintain the melt at 60° to 65° C., the phosphorus pentoxide was added in small increments to the melted heel, with gentle stirring. The stirring speed was increased gradually as more phosphorus pentoxide was added, and the mixture became thicker. The time required for the phosphorus pentoxide addition was 5 minutes. In some cases, a mild exotherm, 5°–10° C., was observed, while in other runs no exotherm was observed at all.

After complete addition of phosphorus pentoxide, the reaction mixture was a thick, easily stirred paste of light tan color. The mixture was heated at 80° C. for addition of stearyl alcohol, and the color was observed to darken slightly.

Stearyl alcohol, 121.5 grams, was then added to a water jacketed addition funnel and melted at 75° to 80° C. The heating mantle was then lowered away from the reaction flask. With stirring, the melted stearyl alcohol was added to the reaction mixture at such a rate that the reaction temperature was maintained at 80° to 85° C. The reaction was exothermic but easily controlled by the rate of addition. The time required for the total addition was 30 minutes.

As more stearyl alcohol was added, the reaction mixture became thinner and lighter tan in color. The increase in volume of the reaction mixture and its fluffy appearance indicated that a considerable amount of air was stirred into the mixture. After complete addition of the alcohol, the light tan mixture was about 500 milliliters in volume. Some brown chunks of solids were observed. The heating mantle was raised, and the mixture was stirred vigorously at 85° C. for 2 hours.

At the end of the stirring period, the reaction mixture was a light pink-brown color. All of the solid chunks had dissolved. The heating mantle was lowered to cool the reaction mixture to 80° C., and 3 grams of distilled water was then added. This was followed by addition of 1.5 gram of 30 percent of hydrogen peroxide. A mild exotherm of 85° to 90° C. was observed. The addition took 1 to 2 minutes. Upon adding water, some solid particles were seen; on stirring they slowly dissolved.

The heating mantle was raised, and the reaction mixture was vigorously stirred at 85° C. for 2 hours. During this period, all solid lumps slowly dissolved.

After the 2-hours stirring, the product was an off-white to light tan liquid paste. Since a flaker was not available in the laboratory, a simple procedure was used to simulate flaking. This was accomplished by pouring a thin film of the product onto a glass plate, allowing the product to cool on the plate at room temperature, and breaking up the product into small flakes with a spatula.

This reaction procedure was repeated several times utilizing either the heel from Experiment 1 or the heel from a process according to Experiment 2. The composition of the products was determined by titration, and the following results were achieved:

| EXPERIMENT | PRODUCT COMPOSITION BY TITRATION | | |
|---|---|---|---|
| | % MONO-Stearyl Acid Phosphate | % di-Stearyl Acid Phosphate | %H$_3$PO$_4$ |
| 2a | 76.8 | 16.1 | 6.3 |
| 2b | 81.5 | 12.5 | 5.2 |
| 2c | 84.1 | 20.5 | 3.9 |
| 2d | 82.2 | 29.6 | 2.9 |

EXAMPLE 3

50 grams of the heel from Example 2 was added to a round-bottom flask provided with a heating mantle and melted at 70° to 75° C. with no stirring. This resulted in a cool dark brown melt with bubbles on top. Gentle stirring was used to dissipate the bubbles. Time required to melt the heel was 20 minutes.

Phosphorus pentoxide, 35.5 grams, was poured into a made-jointed Erlenmeyer flask. The flask was attached to a flexible connector fitted in one neck of the reaction flask. The heating mantle surrounding the reaction flask was set for 80° C. When the heel reached 80° to 85° C., approximately one quarter of the phosphorus pentoxide was added. The addition took 2 minutes. Little change in color or viscosity was observed. The reaction was exothermic, reaching a high of 90° C. within 1 minute after complete addition of one quarter of the phosphorus pentoxide.

As soon as the temperature reached 90° C., approximately 30 grams of stearyl alcohol flakes were added slowly. The reaction mixture cooled immediately. It was important to add flaked stearyl alcohol in a fine stream to avoid formation of lumps of unreacted alcohol which become coated with the reaction mixture. When the lumps are formed, the time required for the alcohol to melt and react doubled.

It was also important to add the alcohol at a slow rate to maintain the pot temperature above 75° C. At lower temperatures, the mixture thickened and caused stirring problems. Time required for complete addition of one quarter of the alcohol was 4 minutes. All of the alcohol was melted within 1 minute after complete addition. The reaction mixture was a light brown, easily stirred liquid. Once the alcohol melted and started reacting with phosphorus pentoxide the reaction was exothermic, heating the mixture back up to 75°-80° C. within 2 minutes.

When the pot temperature reached 75°-80° C., the second one quarter of the phosphorus pentoxide was added over a period of 2 minutes. Little change in color or viscosity was observed. Again, the reaction was exothermic, reaching 90° C., within 1 minute after complete addition of one quarter of the phosphorus pentoxide.

At 90° C., the second quarter of the alcohol was added at such a rate that, after complete addition, the pot temperature was about 75° C., (time required was 3 minutes). The mixture was now an easily stirred thin paste. Stirring speed was gradually increased as the volume became larger.

At 75°-80° C., the third quarter of the phosphorus pentoxide was added in 2 minutes. The temperature was 90° C., at the end of the addition.

At 90° C., the third quarter of the alcohol was added. After complete addition (about 2 minutes) the temperature was 75° C. and rose to 78°-80° C. in 2 minutes.

At 78°-80° C., the remaining phosphorus pentoxide was added over a 2-minute period, reaching a temperature of 90° C.

The remaining alcohol was added in 2 minutes. The reaction mixture cooled to 75° C., but after total melting, it quickly rose back to about 80°-85° C. The heating mantle was adjusted to 85° C., and the mixture stirred vigorously at 85° C. for 2 hours. The reaction mixture was a light to medium brown in color and about 300 milliliters in volume.

At the end of the 2-hour stir period, the reaction mixture was a light tan to pink-brown color, approximately 500 milliliters in volume. A mixture of 3 grams of distilled water and 1.5 gram of 30 percent hydrogen peroxide was then added over a 3-minute period. A mild exotherm to about 90° C. was observed. The color immediately changed to a lighter tan. The reaction mixture was stirred at 80° C. for 2 hours. After the 2-hour stir period, the product was an off-white to a light tan liquid paste. The product was then flaked.

Two variations on the above described procedure were then carried out. They were as follows:

b. All of the phosphorus pentoxide was added to the heel followed by addition of alcohol flakes and stirring for 2 hours at 80°-85° C. Water and hydrogen peroxide were then added, and the mixture was stirred for another 2 hours.

c. One quarter installments of phosphorus pentoxide, stearyl alcohol, hydrogen peroxide, and water were added to the heel until the addition was completed. The mixture was stirred at 80° to 85° C. for 2 hours and then flaked.

The results of Example 3 and the two variations are as follows:

| Procedure | PRODUCT COMPOSITION BY TITRATION | | |
|---|---|---|---|
| | % mono-stearyl acid phosphate | % di-stearyl acid phosphate | %H$_3$PO$_4$ |
| Experiment 3 | 88.8 | 10.6 | 3.3 |
| Variation B | 84.2 | 17.2 | 4.0 |
| Variation C | 88.9 | 18.9 | 2.9 |

The first procedure, conducted according to Example 3, was the most favorable. Variation B resulted in a reaction mixture that was more viscous, and Variation C was characterized by a highly exothermic water addition step that was followed by another exothermic step, the addition of phosphorus pentoxide. The procedure of Variation C was too temperature sensitive.

Having set forth the general nature and some examples of the present invention, the scope is now particularly set forth in the appended claims.

What is claimed is:

1. A method of preparing mono-alkyl acid phosphates having the formula:

wherein R is straight or branched alkyl having from 1 to about 25 carbon atoms, comprising the steps of (1) contacting P$_2$O$_5$ with a heel, wherein said heel is comprised of monoalkyl acid phosphate, di-alkyl acid phosphate and H$_3$PO$_4$; (2) contacting an alcohol having the formula:

ROH wherein R is as defined above, with the P$_2$O$_5$ and heel mixture; followed by mixing until an intermediate is formed having the formula:

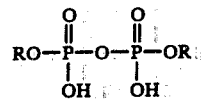

wherein R is as defined above, and then (3) addition of water, followed by mixing until the reaction is complete.

2. The method of claim 1 further comprising the final step of adding H$_2$O$_2$ to the reaction mixture following the addition of water.

3. The method of claim 2 wherein the reaction temperature is maintained from about 20° C. to about 180° C. prior to the addition of water and from about 40° C. to about 200° C. following the addition of water and H$_2$O$_2$.

4. The method of claim 2 wherein R is selected from the group consisting of methyl, ethyl, propyl, isopropyl, butyl, tert-butyl, pentyl, heptyl, octyl, decyl, dodecyl, hexadecyl, nonadecyl, lauryl, palmityl, and stearyl.

5. A method of preparing mono-stearyl acid phosphate comprising the steps of (1) contacting P$_2$O$_5$ with a heel, wherein said heel is comprised of mono-stearyl acid phosphate, di-stearyl acid phosphate and H$_3$PO$_4$; (2) contacting stearyl alcohol with the P$_2$O$_5$ and heel mixture and heating the reactants to a temperature sufficient to melt the stearyl alcohol and mixing while maintaining a reaction temperature sufficient to prevent solidification of said stearyl alcohol until an intermediate is formed having the formula:

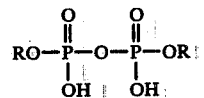

wherein R is stearyl, followed by (3) addition of water and H$_2$O$_2$, followed by mixing until the reaction is complete.

* * * * *

UNITED STATES PATENT AND TRADEMARK OFFICE
CERTIFICATE OF CORRECTION

PATENT NO. : 4,126,650
DATED : November 21, 1978
INVENTOR(S) : Francis A. Via and Sophia Y. Liu It is certified that error appears in the above-identified patent and that said Letters Patent are hereby corrected as shown below:

Col. 2, line 5 - "OR—— 2ROP" should be "OR ———⟩ 2ROP"

Col. 2, line 62 - "accompanies" should be "accompanied".

Col. 3, Line 14 - "typicial" should be "typical".

Col. 3, line 24 - "nuculear" should be "nuclear".

Col. 3, line 31 - "comounds" should be "compounds".

Col. 4, line 17 - "phosphrus" should be "phosphorus".

Signed and Sealed this

Third Day of April 1979

[SEAL]

Attest:

RUTH C. MASON
Attesting Officer

DONALD W. BANNER
Commissioner of Patents and Trademarks